US008394923B2

(12) United States Patent
Lebl (10) Patent No.: US 8,394,923 B2
(45) Date of Patent: *Mar. 12, 2013

(54) APPARATUS AND METHOD FOR SEPARATION OF LIQUID PHASES OF DIFFERENT DENSITY AND FOR FLUOROUS PHASE ORGANIC SYNTHESES

(75) Inventor: Michal Lebl, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/470,130

(22) Filed: May 11, 2012

(65) Prior Publication Data

US 2012/0223025 A1    Sep. 6, 2012

Related U.S. Application Data

(63) Continuation of application No. 13/168,131, filed on Jun. 24, 2011, now Pat. No. 8,178,652, which is a continuation of application No. 10/838,582, filed on May 3, 2004, now Pat. No. 7,977,456, which is a continuation of application No. 09/493,741, filed on Jan. 28, 2000, now Pat. No. 6,846,460.

(60) Provisional application No. 60/118,377, filed on Jan. 29, 1999.

(51) Int. Cl.
*A61K 33/00* (2006.01)
(52) U.S. Cl. ..................................... 530/333
(58) Field of Classification Search ................ None
See application file for complete search history.

(56) References Cited

U.S. PATENT DOCUMENTS

| 3,586,484 A | 6/1971 | Anderson |
| 3,712,535 A | 1/1973 | Genese et al. |
| 3,722,789 A | 3/1973 | Kennedy |
| 3,951,334 A | 4/1976 | Fleming et al. |
| 4,236,666 A | 12/1980 | Aeschlimann et al. |
| 4,244,694 A | 1/1981 | Farina et al. |
| 4,285,463 A | 8/1981 | Intengan |
| 4,412,973 A | 11/1983 | Guigan |
| 4,499,052 A | 2/1985 | Fulwyler |
| 4,822,746 A | 4/1989 | Walt |

(Continued)

FOREIGN PATENT DOCUMENTS

| EP | 0269764 | 6/1988 |
| EP | 0392546 | 10/1990 |

(Continued)

OTHER PUBLICATIONS

Abel et al., "Fiber-Optic Evanescent Wave Biosensor for the Detection of Oligonucleotides," Anal. Chem. 68:2905-2912 (1996).

(Continued)

*Primary Examiner* — Thomas Heard
(74) *Attorney, Agent, or Firm* — Knobbe, Martens, Olson & Bear, LLP (57) ABSTRACT

A simple, efficient apparatus and method for separating layers of immiscible or partially miscible liquids useful in methods of high-throughput combinatorial organic synthesis or parallel extraction of large libraries or megaarrays of organic compounds is disclosed. The apparatus and method are useful, whether as part of an automated, robotic or manual system for combinatorial organic synthesis or purification (extraction). In a preferred embodiment, an apparatus and method for separating layers of immiscible or partially miscible liquids compatible with microtiter plate type array(s) of reaction vessels is disclosed. Another application of centrifugation based liquid removal was found for washing the plates in biological assays or synthesis on modified substrates.

28 Claims, 5 Drawing Sheets

No rotation

U.S. PATENT DOCUMENTS

| | | | |
|---|---|---|---|
| 5,002,867 A | 3/1991 | Macevicz |
| 5,028,545 A | 7/1991 | Soini |
| 5,045,047 A | 9/1991 | Hutchuns et al. |
| 5,089,417 A | 2/1992 | Wogoman |
| 5,105,305 A | 4/1992 | Betzig et al. |
| 5,114,864 A | 5/1992 | Walt |
| 5,132,242 A | 7/1992 | Cheung |
| 5,143,853 A | 9/1992 | Walt |
| 5,178,602 A | 1/1993 | Wells |
| 5,186,824 A | 2/1993 | Anderson et al. |
| 5,194,300 A | 3/1993 | Cheung |
| 5,202,418 A | 4/1993 | Lebl et al. |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,254,477 A | 10/1993 | Walt |
| 5,298,741 A | 3/1994 | Walt et al. |
| 5,320,814 A | 6/1994 | Walt et al. |
| 5,338,831 A | 8/1994 | Lebl et al. |
| 5,342,585 A | 8/1994 | Lebl et al. |
| 5,380,489 A | 1/1995 | Sutton et al. |
| 5,494,798 A | 2/1996 | Gerdt et al. |
| 5,496,997 A | 3/1996 | Pope |
| 5,512,490 A | 4/1996 | Walt et al. |
| 5,516,635 A | 5/1996 | Ekins et al. |
| 5,554,516 A | 9/1996 | Kacian et al. |
| 5,565,324 A | 10/1996 | Still et al. |
| 5,573,909 A | 11/1996 | Singer et al. |
| 5,633,972 A | 5/1997 | Walt et al. |
| 5,679,773 A | 10/1997 | Holmes |
| 5,690,894 A | 11/1997 | Pinkel et al. |
| 5,707,331 A | 1/1998 | Wells et al. |
| 5,770,157 A | 6/1998 | Cargill |
| 5,888,723 A | 3/1999 | Sutton et al. |
| 5,900,481 A | 5/1999 | Lough et al. |
| 6,045,755 A | 4/2000 | Lebl et al. |
| 6,045,760 A | 4/2000 | Aizawa et al. |
| 6,063,596 A | 5/2000 | Lal et al. |
| 6,121,054 A | 9/2000 | Lebl |
| 6,420,437 B1 | 7/2002 | Mori et al. |
| 6,846,460 B1 | 1/2005 | Lebl |

FOREIGN PATENT DOCUMENTS

| | | |
|---|---|---|
| EP | 0 445 915 | 9/1991 |
| EP | 0478319 | 4/1992 |
| EP | 0 569 115 | 11/1993 |
| EP | 0723146 | 7/1996 |
| FR | 2 156 5119 | 6/1973 |
| GB | 1241539 | 8/1971 |
| JP | 61/139756 | 6/1986 |
| JP | 64/083153 | 3/1989 |
| JP | 9/024300 | 1/1997 |
| JP | 11/271227 | 10/1999 |
| WO | WO 89/11101 | 11/1989 |
| WO | WO 90/05590 | 5/1990 |
| WO | WO 92/09300 | 6/1992 |
| WO | WO 93/02360 | 2/1993 |
| WO | WO 93/10455 | 5/1993 |
| WO | WO 96/11878 | 4/1996 |
| WO | WO 97/14028 | 4/1997 |
| WO | WO 97/40385 | 10/1997 |
| WO | WO 98/40726 | 9/1998 |
| WO | WO 98/53093 | 11/1998 |
| WO | WO 98/53300 | 11/1998 |
| WO | WO 99/09394 | 2/1999 |
| WO | WO 99/25470 | 5/1999 |
| WO | WO 99/34931 | 7/1999 |
| WO | WO 00/44491 | 8/2000 |

OTHER PUBLICATIONS

Bangs, L.B., "Immunological Applications of Microspheres," The Latex Course, Bangs Laboratories (Calmel, IN) Apr. 1996.
Barnard et al., "A Fibre-Optic Chemical Sensor with Discrete Sensing Sites," Nature 353-338-340 (Sep. 1991).
Birr, C., Aspects of the Merrifield Peptide Synthesis, Springer-Veriag: New Youk, NY. (1978), entire book, 101 pages.
Drmanac, R. et al., "Prospects for a Miniaturized, Simplified and Frugal Human genome Project," Scientia Yugoslavica 16(1-2):97-107 (1990).
Drmanac, R. et al., "Sequencing by Hybridization (SBH) with Oligonucleotide Probes as an Integral Approach for the Analysis of Complex genomes," International Journal of Genome Research 1(1):59-79 (1992).
Drmanac, R. et al., "Sequencing by Hybridization," Automated DNA Sequencing and Analysis, ed. M. Adams, C. Fields and J. Venter. (1994).
Drmanac, R. et al., "Sequencing by Oligonucleotide Hybridization: A Promising Framework in Decoding of the Genome Program," The First International Conference on Electrophoresis, Supercomputing and the Human Genome, Proceeding of the Apr. 10-13, 1990 Conference at Flordia State University. Ed. C. Cantor and H. Lim.
Fathi, R., et al., "Synthesis and properties of combinatorial libraries of phosphoramidates," J. Org. Chem. 61(16):5600-5609 (1996).
Fodor, S., et al., "Light-directed, spatially addressable parallel chemical synthesis," Science 251(4995);767-773 (Feb. 1991).
Foust, A., et al., Principles of Unit Operations, John Wiley &Sons; New York, NY, p. 628: (1980).
Fuh et al., "Single Fibre Optic Fluorescence pH Probe," Analyst 112:1159-1163 (1987).
Grazia et al., "In-Vivo Biomedical Monitoring by Fiber-Optic Systems," Journal of Lightwave Technology 13(7):1396-1406 (1995).
Healey et al., "Fiberoptic DNA Sensor Array Capable of Detecting Point Mutations," Analytical Biochemistry 251:270-279 (1997).
Hirschfeld et al., "Laser-Fiber-Optic 'Optrode' for real Time in Vivo Blood Carbon Dioxide Level Monitoring," Journal of Light wave Technology LT-5(7):1027-1033 (1987).
Jacobs, J., et al., "Combinatorial chemistry—applications of light-directed chemical synthesis," Trends Biotechnol. 12(1):19-26 (Jan. 1994).
Lebl, M., "A New Approach to Automated Solid Phase Synthesis Based on Centrifugation of Tilted Plates," Journal of the Association for Laboratory Automation 3(3):59-61 (1998).
Lebl, M., "New Technique for High-Throughput Synthesis," Bioorganic & Medicinal Chemistry Letters 9:1305-1310 (1999).
Marziali et al "An Arrayable Flow-Through Microcentrifuge for High-Throughput Instrumentation", Published online Jan. 2, 1999, PNAS, pp. 61-66.
McDevitt, J., et al., "Glycosamino acids: new building blocks for combinatorial synthesis," J, Am. Chem. Soc. 118(16):3818-3828 (Apr. 1996).
Menotti et al., Facile Manual Synthesis of Peptide Libraries, Protein and Peptide Letters 1(3):187-192 (1994).
Peterson, J. et al., "Fiber Optic PH Probe for Physiological Use," Anal. Chem. 52:864-869, (1980).
Peterson et al., "Fiber-Optic Sensors for Biomedical Applications," Science 13:123-127 (1984).
Piunno et al., "Fiber-Optic DNA Sensor for Fluorometric Nucleic Acid Determination," Anal. Chem. 67:2635-2643 (1995).
Plunkett, M., et al., "Combinatorial chemistry and new drugs," Sci. Am. 276(4):69-73 (Apr. 1997).
Pope, E. "Fiber Optic Chemical Microsensors Employing Optically Active Silica Microspheres," SPIE, 2388:245-256 (1995).
Ruvo, M., et al., "Facile manual synthesis of peptide libraries," Prot. Peptide Lett. 1(3):187-192 (1994).
Still, W.C., et al., "Discovery of sequence-selective peptide binding by synthetic receptors using encoded combinatorial libraries," Acc. Chem. Res 29(3):155-163 (1996).
Strachan, et al., "A Rapid General Method for the identification of PCR Products Using a Fiber-Optic Biosensor and its Application to the Detection of Listeria," Letters in Applied Microbiology, 21:5-9 (1995).

Zhang, C., et al., "A combinatorial method for the solid phase synthesis of a-amino phosphates and phosphonic acids," Tet. Lett. 37(31):5457-5460 (Jul. 1996).

Anonymous, "Fluorescent Microspheres," Tech. Note 19, Bang Laboratories, (Fishers, In.) Feb. 1997.

Anonymous, "Microsphere Selection Guide," Bandg Laboratores, (Fisher, In.) Sep. 1998.

Spyder Technology "A New Approach to Automated Solid Phase Synthesis Based on Centrifugation of Tilted Plates" [online], Feb. 1, 1999, [retrieved on Nov. 6, 2006. Retrieved from the internet: URL:http://www.5z.com/spyder/technology3.html.

Wizard PCR Preps DNA Purification Technical Bulletin Part # TB118 Jun. 1997 pp. 1-8.

FIG. 1A No rotation
FIG. 1B Low speed
FIG. 1C High speed

APPARATUS AND METHOD FOR SEPARATION OF LIQUID PHASES OF DIFFERENT DENSITY AND FOR FLUOROUS PHASE ORGANIC SYNTHESES

CROSS-REFERENCE TO RELATED APPLICATIONS

This application is a continuation of U.S. patent application Ser. No. 13/168,131, entitled APPARATUS AND METHOD FOR SEPARATION OF LIQUID PHASES OF DIFFERENT DENSITY AND FOR FLUOROUS PHASE ORGANIC SYNTHESES, filed Jun. 24, 2011, which is a continuation of U.S. patent application Ser. No. 10/838,582, entitled APPARATUS AND METHOD FOR SEPARATION OF LIQUID PHASES OF DIFFERENT DENSITY AND FOR FLUOROUS PHASE ORGANIC SYNTHESES, filed May 3, 2004 and issued Jul. 12, 2011 as U.S. Pat. No. 7,977,456, which is a continuation of U.S. patent application Ser. No. 09/493,741, entitled APPARATUS AND METHOD FOR SEPARATION OF LIQUID PHASES OF DIFFERENT DENSITY AND FOR FLUOROUS PHASE ORGANIC SYNTHESES, filed Jan. 28, 2000 and issued Jan. 25, 2005 as U.S. Pat. No. 6,846,460, which is a nonprovisional application of U.S. Provisional Patent Application No. 60/118,377, filed Jan. 29, 1999, the entire contents of which is incorporated herein by this reference.

FIELD OF INVENTION

The present invention relates to the field of devices and methods for chemical synthesis, analysis, and biological screening. More particularly, the present invention relates to a simple efficient apparatus and method for separation of immiscible or partially miscible liquid phases of different density in high-throughput, organic synthesis, or for removal of liquid from the vessels (washing). The present invention is particularly applicable for high-throughput combinatorial synthesis of organic molecules, whether as part of an automated or a manual procedure.

BACKGROUND OF THE INVENTION

Solid phase synthesis of organic molecules is the method of choice for preparation of libraries and compound megaarrays, which are currently being applied for screening in the quest to find new drugs or pharmaceutical lead compounds, i.e., compounds which exhibit a particular biological activity of pharmaceutical interest, and which can serve as a starting point for the selection and synthesis of a drug compound, which in addition to the particular biological activity of interest has pharmacologic and toxicologic properties suitable for administration to animals, including humans.

Fluorous synthesis is in its principle similar to solid phase synthesis. In fluorous synthesis the certain component of the reaction (starting material, reagent, or product) is preferentially retained in the fluorine atoms containing phase due to its high content of fluorine atoms. Fluorous phase is usually the high density one and therefore it can be separated as the lower phase in the multiphase system. Manual synthesis requires repetitions of several relatively simple operations of addition of reagents, incubation and separation of liquid phases. This character of the synthetic process renders it optimal for automation.

Several designs of automated instruments for combinatorial synthesis utilizing solid phase synthesis have appeared in the patent and non-patent literature. However, there is no instrument designed for the fluorous synthesis, since the simple principle of separation of phases by filtration is not applicable.

The productivity of automated instruments can be dramatically improved by use of disposable reaction vessels (such as multititer plates or test tube arrays) into which reagents are added by pipetting, or by direct delivery from storage containers. The optimal storage vehicle is a syringe-like apparatus of a material inert to the chemical reactants, etc., e.g., a glass syringe, allowing the storage of the solution without any exposure to the atmosphere, and capable of serving as a delivery mechanism at the same time. See U.S. Pat. No. 6,045,755. An alternative technique based on the removal of upper layer of liquid by suction from the surface above the separated layers is limited to the arrays of up to a hundred of suction needles. (For similar situation in solid phase synthesis see U.S. Pat. No. 6,045,755). The present application is an improvement upon U.S. Pat. Nos. 5,202,418, 5,338,831, 5,342,585, and 6,045,755 which describe placement of resin in polypropylene mesh packets and removal of liquid through the openings of these packets, or removal of the liquid from the pieces of porous textile-like material by centrifugation. or removal of liquid phase from the solid phase by centrifugation of tilted plates. liquid removal by centrifugation was described and is the subject of several publications (see the book "Aspects of the Merrifield Peptide Synthesis" by Christian Birr in the series Reactivity and Structure Concepts in Organic Chemistry vol. 8, K. Hafner, J.-M. Lehn, C. W. Rees, P. von Rague, Schleyer. B. M. Trost, R. Zahradnik, Eds., Sringer-Verlag, Berlin, Heidelberg, New York, 1978, and German Patent Application P 20 17351.7, G. 70 13256.8, 1970. These references describe the use of centrifugation for liquid removal from slurry of solid phase particles in a concentric vessel equipped with a filtration material in its perimeter and spun around its axis. See also WO99/25470, hereby expressly incorporated by reference in its entirety.

None of the prior art contemplates the separation of two (or more) immiscible, or partially miscible liquids of different density by removal of lighter layers of liquids by creation of "pockets" from which material cannot be removed by centrifugal force. This technique can be used in situations where multiplicity of products are to be extracted in parallel (e.g. in parallel purification of products of combinatorial synthesis). However, there is a need for a simple, efficient means of separating liquid phases during fluorous phase synthesis of organic molecules, particularly a method amenable to use with automated methods for such syntheses.

Furthermore, complete removal of the liquid from the multiplicity of vessels by spinning the array of wells attached with "reverse tilt" (tilting away from the axis of rotation) can find its application in biological assays where fast repeated washings of surface bound reagents or cells are required, and in applications where synthesis is done directly on the surface of the reaction vessels.

SUMMARY OF THE INVENTION

In accordance with the above objects, the present invention provides methods for elimination of a liquid phase from reaction vessels comprising positioning a plurality of reaction vessels containing a liquid or mixture of liquids in a holder on the perimeter of a centrifuge rotor. The holder, and thus the reaction vessels, are held in a tilted position with a tilt away from the axis of rotation. The rotor is then spun at a speed that expels the liquid from the vessels. This method of elimination can be used during solid-phase organic synthesis, for example synthesis of peptides or nucleic acids. Optionally, these steps can be repeated. Similarly, the reaction vessels may be contained in a microtiter plate or the reaction vessel may be a microtiter plate.

The expelled liquid can be collected in a collection pocket in the holder having a volume sufficient to collect and retain any liquid expelled from the vessels, or can be collected in a waste reservoir in or outside of the centrifuge.

In an additional aspect, the invention provides methods of synthesis of compounds comprising providing a reaction vessel containing a first building block coupled to the vessel itself. The vessel is then positioned in a holder on the perimeter of a centrifuge rotor. A second building block is added to the vessel under conditions that allow the coupling of the first and second building blocks, and the rotor is spun at a speed sufficient to expel the liquid from the vessel. Optional additional steps of repeating the procedure or washing steps can also be included. The building blocks can include amino acids and nucleosides.

In a further aspect, the invention provides methods for separating at least two immiscible or partially miscible liquids comprising positioning a plurality of reaction vessels containing the liquids in a holder on the perimeter of a centrifuge rotor. The rotor is then spun at a speed such that the lower layer of the multi phase system is retained in a "pocket" of the vessels and the upper layer is expelled from the vessels.

In an additional aspect, the invention provides apparatus comprising a centrifuge comprising a rotor designed to hold reaction vessels at a tilt away from the axis of rotation and a waste reservoir connected to the centrifuge to hold liquids expelled from the reaction vessels. In one embodiment, the waste reservoir is connected to the centrifuge with a tube. The apparatus may optionally comprise a liquid distribution system and a computer processor.

BRIEF DESCRIPTION OF THE DRAWINGS

The present invention can be understood more completely by reference to the following detailed description, examples, appended claims and accompanying figures.

FIG. 1A illustrates the lower liquid phase and upper liquid phase in the vessel prior to centrifugation. FIGS. 1B and 1C illustrate the pocket containing retained lower liquid phase layer during spinning (and removal of the upper liquid layer).

DETAILED DESCRIPTION OF THE INVENTION

For clarity of disclosure, and not by way of limitation, the detailed description of this invention is presented herein with respect to figures that illustrate preferred embodiments of elements of this invention. However, this invention includes those alternative embodiments of these elements performing similar functions in similar manners that will be apparent to one skilled in the art from the entirety of the disclosure provided. In addition, all references disclosed herein are incorporated by reference in their entirety.

The present invention is based on a discovery of a simple efficient means for separation of two (or more) immiscible, or partially miscible liquids of different density, e.g., removal of upper layer or layers of liquid from lower layer: used for parallel extraction and/or in fluorous phase organic syntheses. In one embodiment of the invention, the fluorous phase organic synthetic protocol utilizes widely available, disposable reaction vessel arrays, such as microtiter style plates. In an alternative embodiment of the invention, the synthetic protocol utilizes a vessel with a lip facing inward (see FIG. 2) spun around its axis to create a "pocket" in which the lower layer of the multiphase system is retained. According to the present invention, however, any vessel or array of vessels or plurality of arrays of vessels which can be placed in a tilted position on the perimeter of a centrifuge, can be used in the method of the invention. The method of the invention for separating of two (or more) immiscible, or partially miscible liquids of different density during a parallel extraction and/or in fluorous phase organic synthetic process comprises: (1) positioning a reaction vessel or an array of reaction vessels, such as a microtiter plate having an array of reaction wells, said vessel(s) containing a multilayer system of liquid phases, on the perimeter of a centrifuge rotor in a tilted position; and (2) spinning the rotor of the centrifuge at a speed so that the lower layer fills a "pocket" of the vessels and the upper liquid phases are expelled from the vessels. In one embodiment of the invention, the rotor is spun at a speed so that the centrifugal force on the radius corresponding to the reaction vessels which are closest to the axis of rotation is significantly greater than the force of gravity, and the lower layer forms a "pocket" of the vessels and the upper layers are expelled from the vessels. The volume of a "pocket" is determined by: (i) the degree of the tilt, (ii) the speed of rotation, and (iii) the distance of the particular reaction vessel from the axis of rotation. The appropriate combination of these factors determines the volume of residual liquid retained in the pocket and therefore completeness of upper layer removal. However, since it is desired that all reaction vessels in a multivessel arrangement of a reaction block (such as a microtiter plate) should undergo the removal of the upper layers of liquid to the same degree, it is important that the angle of the liquid surface in the "pocket" of the reaction vessels during the centrifugation is as close to 90 degrees with respect to the center of rotation as possible. In one embodiment, the removed liquid phase is collected on the wall of the centrifuge. In an alternative embodiment, the removed liquid phase is collected in a "collecting pocket" or a series of "collecting pockets" attached at the perimeter of the centrifuge rotor. The apparatus of the invention comprises a holder adapted to attaching a reaction vessel or an array of reaction vessels, e.g., a microtiter plate, to a rotor of a centrifuge, said holder comprising one or more indentations or groves designated "collecting pockets" positioned along one side of said holder said collecting pockets having a volume sufficient to collect and retain any liquid expelled from the reaction vessels, e.g., the wells of the microtiter plate, when the holder and attached reaction vessels are spun by the centrifuge rotor. According to the invention, the holder can hold a single or individual microtiter plate or a plurality of microtiter plates, each plate comprising an array of vessels. One or more of the holders can be attached to the rotor of a centrifuge. In another embodiment, the apparatus of the invention is an automated integrated apparatus or system for parallel extraction and/or for fluorous phase chemical synthesis, comprising: (a) a centrifuge in which an array of reaction vessels suitable for parallel extraction and/or for fluorous phase organic synthesis can be spun in a tilted position; (b) a liquid distribution device; and (c) a computer for processing a program of instructions for addition of liquid phase to and removal, via centrifugation, of upper layer liquid phase from the reaction vessels, according to the program.

In general, the methods and apparatus of the invention find use in combinatorial chemical synthesis. By way of introduction, combinatorial chemistry synthesis protocols prescribe the stepwise, sequential addition of building blocks to intermediate and/or partially synthesized intermediate compounds in order to synthesize a final compound. In solid-phase synthesis, final compounds are synthesized attached to solid-phase supports that permit the use of simple mechanical means to separate intermediate, partially-synthesized intermediate compounds between synthetic steps. Typical solid-phase supports include beads, including microbeads, of 30 microns to 300 microns in diameter, which are functionalized in order to covalently attach intermediate compounds (or final compounds), and made of, e.g., various glasses, plastics, or resins.

WO 99/25470, hereby incorporated by reference, describes the use of a centrifuge in solid-phase synthetic reactions, wherein particles of solid phase (microbeads) are contained in reaction vessels such as microtiter plates. Synthesis is achieved by the stepwise addition of "building blocks" of the biopolymer, followed by centrifugation that drives the liquid phase out of the reaction vessels yet traps the solid phase in "pockets".

This general idea can be applied to differential phase synthetic reactions as well. While described for fluorous synthesis, one of skill in the art will appreciate that these techniques work for other phase-dependent synthetic methods as well.

The principle of fluorous phase synthesis is very similar to solid phase synthesis. In fluorous phase synthesis one of the reagents is attached to a high fluorine content block ("fluorous tail"), which assures that this reactant will always have a tendency to stay in fluorocarbon based solvent layer. Due to the fact that some fluorocarbon based solvents are not miscible (or only partially miscible) with both organic solvents and water and that this phase is in most cases the phase with the highest density, its properties can be used to mimic the solid phase principle of synthesis. Due to the fact that fluorous phase synthesis technology is at its very early stage of development, the general process for application in the combinatorial synthesis can be only speculated on. Fluorous phase combinatorial synthesis should proceed according to the following steps. In a first step, reaction vessels are charged with a fluorous base, e.g. benzotrifluoride, and the first component of the synthesis (sometimes referred to herein as "the first building block") with attached "fluorous tail" (block containing high proportion of fluorine atoms) is delivered to all wells. Subsequently, a plurality of building block addition steps are performed, all of which involve repetitive execution of the following substeps, and in a sequence chosen to synthesize the desired compound. First, a sufficient quantity of a solution containing the building block moiety (e.g. the "second building block", "third building block", etc.) selected for addition is accurately added to the reaction vessels so that the building block moiety is present in a molar excess to the intermediate compound (compound with fluorous tail). The reaction is triggered and promoted by activating reagents and other reagents and solvents, which are also added to the reaction vessel. The reaction vessel is then incubated at a controlled temperature for a time, typically between 5 minutes and 24 hours, sufficient for the building block addition reaction or transformation to go to substantial completion. Optionally, during this incubation, the reaction vessel can be intermittently agitated or stirred. Finally, in a last substep of building block addition, the reaction vessel containing the fluorous phase with intermediate compound attached to fluorous tail is prepared for addition of the next building block by removing the reaction fluid and thorough washing and reconditioning the fluorous phase by washing (repetitive addition and removal by centrifugation) with water and/or organic solvents. The limitation is that the fluorous phase must form always the lower phase of the system, which can be multilayer (multiphase).

Washing typically involves three to seven cycles of adding and removing a wash solvent. Optionally, during the addition steps, multiple building blocks can be added to one reaction vessel in order to synthesize a mixture of compound intermediates attached to one fluorous tail, or alternatively, the contents of separate reaction vessels can be combined and partitioned in order that multiple compounds can be synthesized in one reaction vessel.

After the desired number of building block addition steps, the final compound is present in the reaction vessel attached to the fluorous tail. The final compounds can be utilized either directly attached to the fluorous tail, or alternatively, can be cleaved from the fluorous tail and purified by extraction. Examples of fluorous phase synthetic protocols can be found in the following references: Curran, D. P. (1996) Combinatorial organic synthesis and phase separation: Back to the future. Chemtracts: Org. Chem., 9, 75-87; Curran, D. P., & Hoshino, M. (1996) Stille couplings with fluorous tin reactants: Attractive features for preparative organic synthesis and liquid-phase combinatorial synthesis. J. Org. Chem., 61, 6480-481; Curran, D. P. (1998) Fluorous synthesis: An alternative to organic synthesis and solid phase synthesis for the preparation of small organic molecules. Canc. J. Sci. Amer., 4, S73-S76; Curran, D. P. (1998) Strategy-level separations in organic synthesis: From planning to practice. Angew. Chem. Int. Ed., 37, 1175-1196; Ogawa, A., & Curran, D. P. (1997) Benzotrifluoride: A useful alternative solvent for organic reactions currently conducted in dichloromethane and related solvents. J. Org. Chem., 62, 450-451; Studer, A., Jeger, P., Wipf, P., & Curran, D. P. (1997) Fluorous synthesis: Fluorous protocols for the Ugi and Biginelli multicomponent condensations. J. Org. Chem., 62, 2917-2924; Studer, A., & Curran, D. P. (1997) A strategic alternative to solid phase synthesis: Preparation of a small isoxazoline library by "fluorous synthesis". Tetrahedron, 53, 6681-696; Studer, A., Hadida, S., Ferritto, R., Kim, S. Y., Jeger, P., Wipf, P., & Curran, D. P. (1997) Fluorous synthesis: A fluorous-phase strategy for improving separation efficiency in organic synthesis. Science, 275, 823-826. As for all the references herein, these are expressly incorporated by reference in their entirety.

Accordingly, in a preferred embodiment, the invention provides methods for separation of immiscible or partially miscible liquid phases of different density during a parallel extraction, including a fluorous phase organic synthetic process. The methods comprise: (1) positioning a reaction vessel or one or more arrays of reaction vessels, such as one or more microtiter plates, said vessels containing an immiscible or partially miscible liquid phases of different density on the perimeter of a centrifuge rotor in a tilted position; and (2) spinning the rotor of the centrifuge at a speed so that the lower phase is retained in a "pocket" of the vessels and the upper liquid phase(s) is (are) expelled from the vessels. In the case where only one row of vessels is placed at the perimeter of the centrifuge rotor, the ratio of centrifugal force versus gravitation determines the volume of the "pocket" used for the separation of liquid phases in all vessels and even very low ratio (such as 1:1) can be successfully used. The important factor is only the reproducibility of the speed of centrifugation.

In one embodiment of the invention, the rotor of the centrifuge is spun at a speed so that the centrifugal force on the radius corresponding to the reaction vessels which are closest to the axis of rotation is significantly greater than the force of gravity so that the lower liquid phase is retained in a "pocket" of the vessels and the upper liquid phase(s) is (are) expelled from the vessels. The volume of a "pocket" is determined by: (i) the degree of the tilt, (ii) the speed of rotation, and (iii) the distance of the particular reaction vessel from the axis of rotation. Since it is desired that all reaction vessels in a multivessel arrangement or array of vessels (such as a microtiter plate) should undergo the removal of the upper liquid phase to the same degree, it is important that the angle of the liquid surface in the "pocket" of the reaction vessels during the centrifugation is as close to 90 degrees with respect to the axis of rotation as possible. As used in the present application, the term "significantly greater than the force of gravity" is intended to mean that the force is at least about 5 to 300×G, preferably about 10 to 300×G, and even more preferably about 100 to 300×G. In other words, the centrifuge is spun at a speed so that the ratio of the centrifugal force to gravity, i.e., the Relative Centrifugal Force (RCF) is at least about 5 to 300, preferably about 10 to 300, and more preferably about 100 to 300. Values of RCF significantly greater than 1 are required if individual vessels are placed at different distances from the center of rotation. To achieve uniform distribution of liquid in all vessels it is important to remove as much as possible of the upper liquid phase from all wells. The theoretical value of an angle of liquid surface achievable in the centrifuge versus liquid in nondisturbed state is 90 degrees. This requires a value of the above mentioned ratio (RCF) reaching infinity. For practical reasons, the difference between 89 degrees (ratio 100:1) or 85 degrees (ratio 18:1) may be acceptable. Acceptability of this value depends on the degree of the tilt determining the absolute value of the "pocket" volume. The greater the tilt, the bigger the "pocket" volume, and the bigger the tolerance to the different ratio values at different radiuses. The maximal possible value of the tilt in "fixed tilt" centrifuges is 45 degrees, however, this tilt is completely impractical because the maximal volume of liquid in the well is equal to the volume of the theoretical "pocket".

Figure 1A:
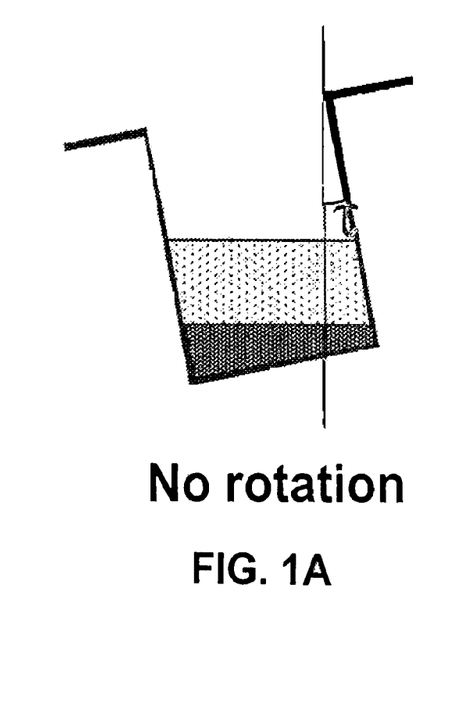
FIGS. 1A, 1B and 1C illustrate separation of two immiscible or partially miscible liquid phases in a "pocket" of the vessels and expulsion of upper liquid layer achieved according to the method of the invention.
Figure 1B:
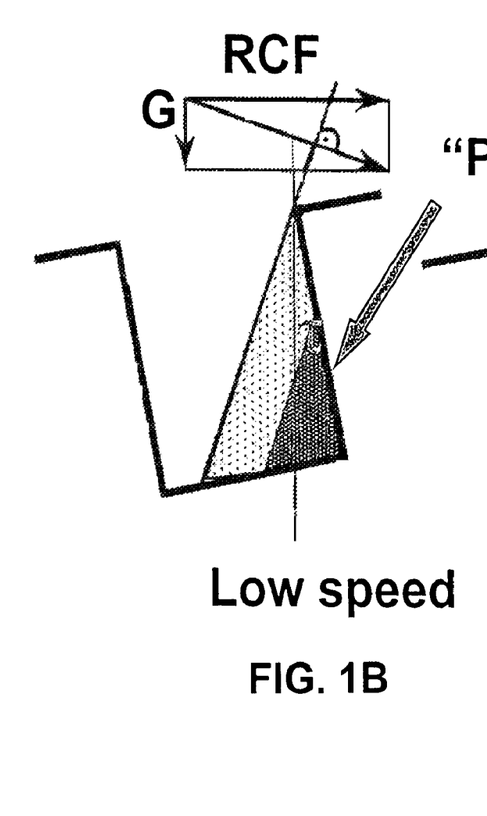
Figure 1C:
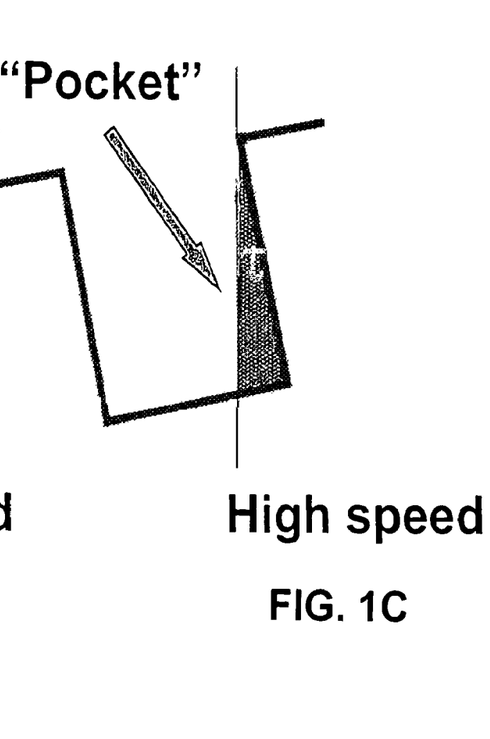
Figure 2A:
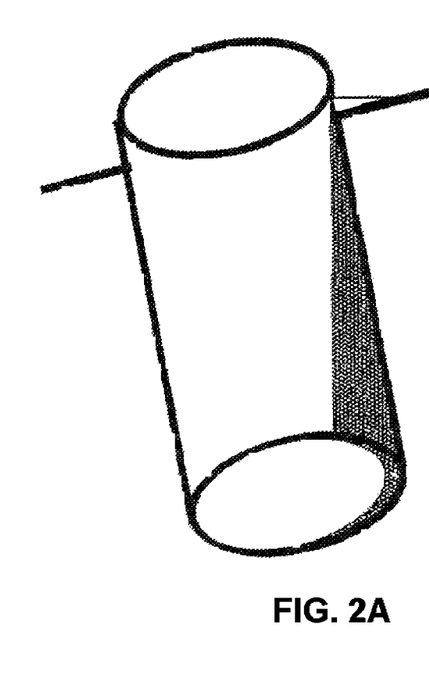
FIGS. 2A, 2B and 2C illustrate the path of liquid removed from a vessel, such as a well of a microtiter plate by centrifugation. The straight lip at the upper end of each well of the microtiter plate prevents the liquid from entering the well closer to the edge of a centrifugal plate—this well is higher and the lip wall is tilted in the direction to the bottom of the plate. The large arrow represents the vector resulting from centrifugal and gravitational forces. The small arrow with thin trailing line illustrates the direction of the flow of liquid removed.
Figures 2B, 2C:
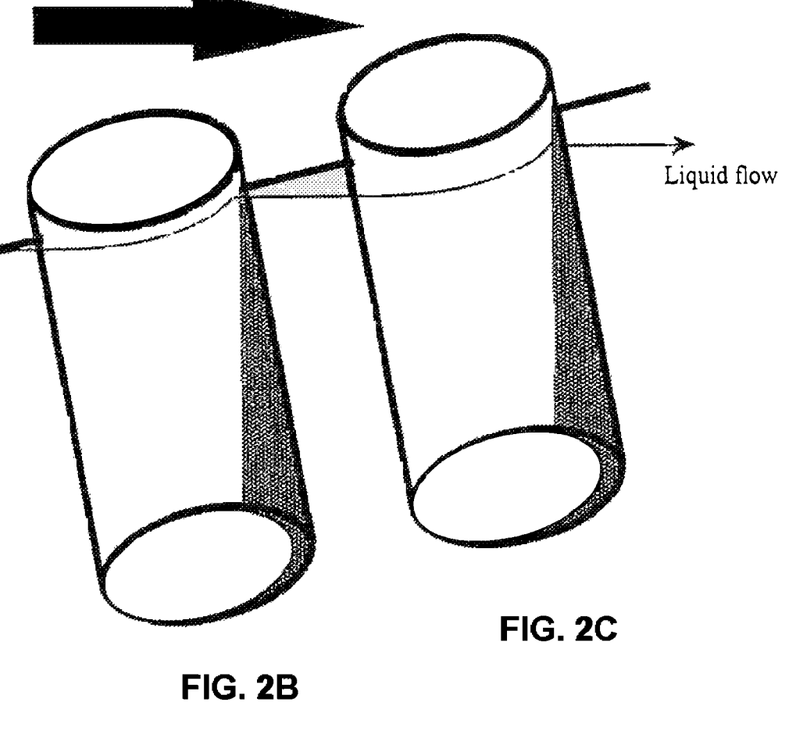
Figure 3A:
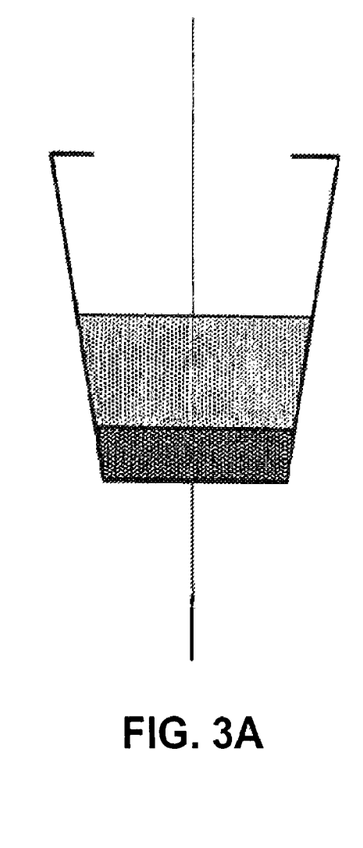
FIGS. 3A and 3B illustrate an alternative embodiment of the invention in which a vessel having a lip facing inward when spun according to the method of the invention "creates" a "pocket" in which the lower liquid phase is retained.
Figure 3B:
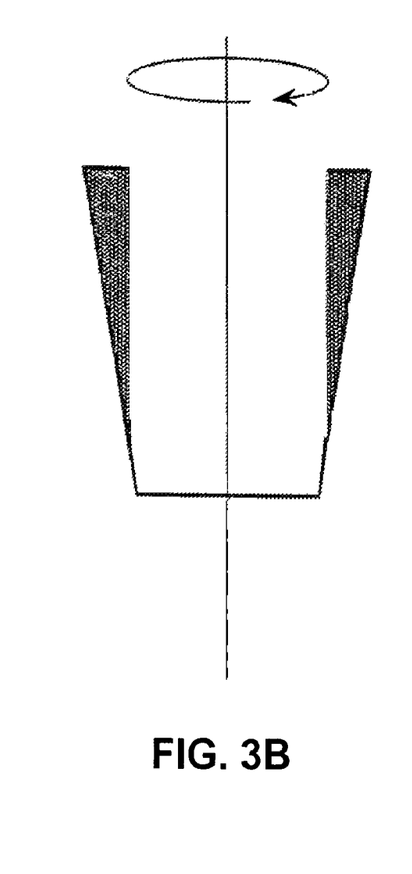
Figure 4A:
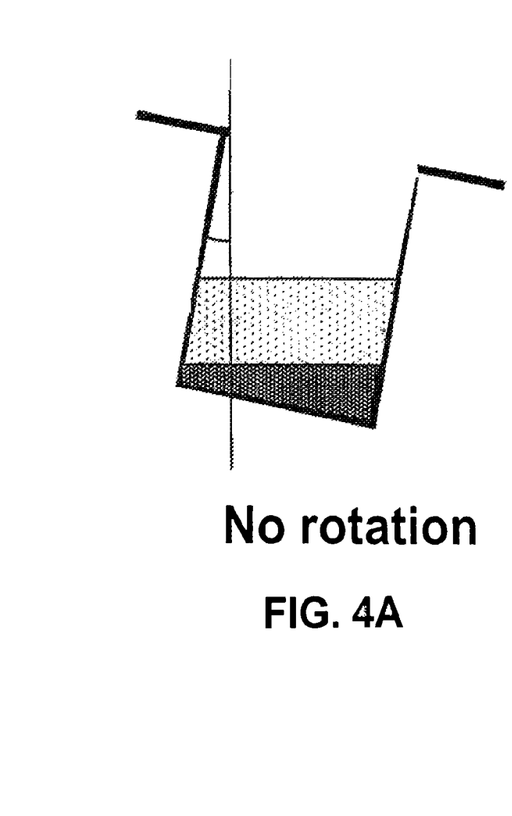
FIGS. 4A, 4B and 4C illustrate the situation in which wells are tilted in "reverse" tilt and no "pocket" is formed during centrifugation. The result is the complete removal of all liquid from the wells.
Figures 4B, 4C:
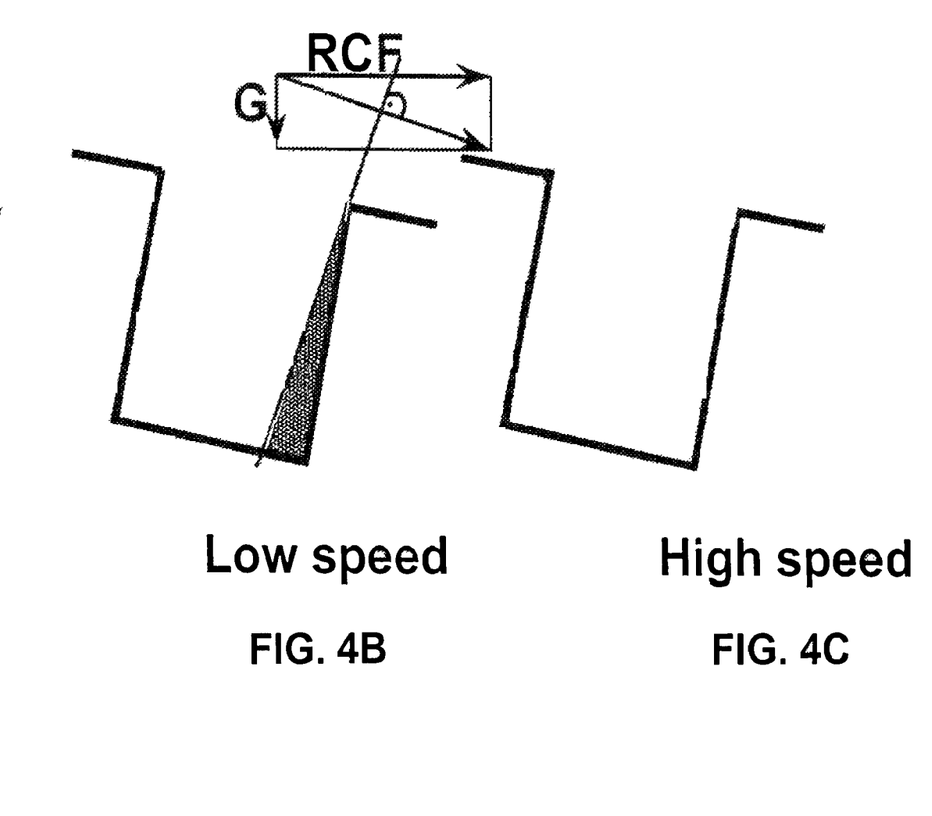

Higher tilt is possible in the case of "dynamically adjustable tilt" centrifuges (centrifuges in which plate is horizontal in standstill state and "swings out" to a limited position during rotation). According to one mode of one embodiment of the method of the invention, when the reaction vessels used are one or more arrays of regular wells in a microtiter plate, the rotor of the centrifuge is spun at a speed so that the centrifugal force on the radius of wells closest to the axis of rotation is about 5 to 300×G, preferably about 10 to 300×G, and more preferably about 100 to 300×G; and the angle of tilt of the plate is about 1 to 45, preferably 5 to 20, and more preferably 5 to 15 degrees. According to another mode of this embodiment of the method of the invention, when the reaction vessels used are one or more arrays of microwells in a microtiter plate, the rotor of the centrifuge is spun at a speed so that the centrifugal force on the radius of wells closest to the axis of rotation is about 5 to 300×G, preferably about 10 to 300×G, and more preferably about 100 to 300×G and the angle of tilt of the plate is about 2 to 25, preferably 2 to 10 degrees. In one embodiment, the upper liquid phase is collected on the wall of the centrifuge. In an alternative embodiment, the upper liquid phase is collected in a "collecting pocket" or a series of "collecting pockets". FIG. 1 illustrate retention of lower liquid layer in a "pocket" of the vessels and expulsion of upper liquid layer achieved according to the method of the invention. FIG. 2 illustrates the path of upper liquid layer removed from a vessel, such as a well of a microtiter plate by centrifugation. The straight lip at the upper end of each well of the microtiter plate prevents the liquid from entering the well closer to the edge of a centrifugal plate—this well is higher and the lip wall is tilted in the direction to the bottom of the plate. The large arrow represents the vector resulting from centrifugal and gravitational forces. The small arrow with thin trailing line illustrates the direction of the flow of liquid removed from the reaction vessels. FIG. 3 illustrates an alternative embodiment of the invention in which a vessel having a lip facing inward when spun according to the method of the invention "creates" a "pocket" in which the lower liquid phase is retained. The left portion of FIG. 1 illustrates the lower liquid phase and upper liquid phase in the vessel prior to centrifugation. The right portion of FIG. 1 illustrates the pocket containing retained lower liquid phase layer during spinning (and removal of the upper liquid layer). As detailed above, a single reaction vessel, a single microtiter plate or a plurality of microtiter plates can be used in the process of the present invention.

In addition to differential phase synthesis, the present invention finds use in "reverse tilt" synthesis reactions. In this embodiment, the reaction vessels, for example in a microtiter plate format, are tilted in the direction away from the axis of rotation: that is, the open end of the reaction vessel is pointed away from the axis of rotation. The negative (or "reverse") tilt (tilt in the direction away from the axis of rotation) allows for the removal of all liquid content of the well. This may be done for a variety of reasons. In a first embodiment, this may be applicable for washing of wells, e.g. in biological assays when binding to the surface (or modified surface) is studied and removal of the excess of the reagents by repetitive washing is required.

A preferred embodiment for the use of "reverse" tilt is the situation wherein the synthesis is performed on material firmly attached to the well; that is, the material will not be expelled from the reaction vessel under the centrifugation conditions used in the process. In a preferred embodiment, the material can be a "tea-bag" type of material filled with the solid support on which the synthesis is done, or a textile like material; for examples of these supports see U.S. Pat. No. 5,202,418, hereby expressly incorporated by reference.

In a preferred embodiment, the synthesis is performed on one or more modified surface(s) of the reaction vessel itself. In this embodiment, rather than use a solid support such as a microbead or a dense phase as the support for a synthetic reaction, the actual surface of the reaction vessel is used as the solid phase for synthetic reactions; liquid reagents are added, reacted, and then the residual liquid is removed via centrifugation. That is, the reaction vessel, such as a microtiter plate, may be functionalized as a solid support for the synthesis. In this embodiment, the reaction vessel may be any material that can be modified to allow synthesis; possible materials for substrates include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides nylon or nitrocellulose, resins, silica or silica-based materials including silicon and modified silicon, carbon, metals, inorganic glasses, and plastics, and a variety of other polymers.

The functionalization of solid support surfaces such as certain polymers with chemically reactive groups such as thiols, amines, carboxyls, etc. is generally known in the art. Some examples of these surface chemistries for subsequent addition of building blocks include, but are not limited to, amino groups including aliphatic and aromatic amines, carboxylic acids, aldehydes, amides, chloromethyl groups, hydrazide, hydroxyl groups, sulfonates and sulfates.

These functional groups can be used to add any number of different building block moieties to the vessels, generally using known chemistries, including, but not limited to the use of amino-functionalized supports, sulfhydryl linkers, etc. There are a number of sulfhydryl reactive linkers known in the art such as SPDP, maleimides, α-haloacetyls, and pyridyl disulfides (see for example the 1994 Pierce Chemical Company catalog, technical section on cross-linkers, pages 155-200, incorporated herein by reference). Similarly, amino groups on the building blocks and on the surface can be attached using linkers;. for example, a large number of stable bifunctional groups are well known in the art, including homobifunctional and heterobifunctional linkers (see Pierce Catalog and Handbook, pages 155-200). In an additional embodiment, carboxyl groups (either from the surface or from the building block) may be derivatized using well known linkers (see the Pierce catalog). For example, carbodiimides activate carboxyl groups for attack by good nucleophiles such as amines (see Torchilin et al., *Critical Rev. Therapeutic Drug Carrier Systems,* 7(4):275-308 (1991), expressly incorporated herein). In addition, preferred methods include systems that allow post-synthesis cleavage from the reaction vessels.

As will be appreciated by those in the art, the functionalization will depend on the synthesis done, as outlined below.

As will be appreciated by those in the art, in the reverse tilt embodiments, virtually any solid phase synthesis reaction may be done. Preferred embodiments include organic syntheses, including, but not limited to, peptide synthesis, nucleic acid synthesis, and small molecule synthesis.

In a preferred embodiment, peptides are synthesized. By "peptide" herein is meant at least two amino acids joined via a peptide bond. The peptide may be made up of naturally occurring amino acids and peptide bonds, or synthetic peptidomimetic structures. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

The stepwise solid phase synthesis of peptides is well known. An exemplary solid-phase combinatorial protocol is that for the synthesis of peptides attached to polymer resin, which proceeds according to Lam et al., 1991, Nature 354: 82-84; U.S. Pat. No. 5,510,240; Lam et al., 1994, Selectide technology: Bead-binding screening. Methods: A Companion to Methods in Enzymology 6:372-380. Another exemplary protocol is that for the synthesis of benzodiazepine moieties, which proceeds according to Bunin et al., 1992, J. Amer. Chem. Soc., 114:10997-10998 and U.S. Pat. No. 5,288,514. Also, for protocols for the addition of N-substituted glycines to form peptoids, see, e.g., Simon, et al., 1992, Proc. Natl. Acad. Sci. USA, 89:9367-9371; Zuckermann et al., 1992, J. Amer. Chem. Soc., 114:10646-10647; WO94/06451 to Moos et al.; Approaches for synthesis of small molecular libraries were recently reviewed by, e.g., Krchnak and Lebl, 1996, Molecular Diversity, 1:193-216; Ellman, 1996, Account. Chem. Res., 29:132-143; Armstrong et al., 1996, Account. Chem. Res., 29:123-131.; Fruchtel et al., 1996, Angew. Chem. Int. Ed., 35:17-42; Thompson et al., 1996, Chem. Rev., 96:555-600; Rinnova et al., 1996. Collect. Czech. Chem. Commun., 61: 171-231; Hermkens et al., 1996, Tetrahedron, 52:4527-4554. Exemplary building blocks and reagents are amino acids, nucleosides, other organic acids, aldehydes, alcohols. and so forth, as well as bifunctional compounds, such as those given in Krchnak and Lebl, 1996, Molecular Diversity. 1:193-216.

In a preferred embodiment, the methods and compositions of the invention are used to synthesize nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below. nucleic acid analogs are included that may have alternate backbones, comprising. for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al. Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al. J. Am. Chem. Soc. 111 :2321 (1989), O-methylphophoroamidite linkages (see Eckstein, Oligonucleotides and Analogues: A Practical Approach. Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et at, J. Am. Chem. Soc. 110:4470 (1988); Letsinger et at, Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et at, Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done to increase the stability and half-life of such molecules in physiological environments.

As will be appreciated by those in the art, all of these nucleic acid analogs may find use in the present invention. In addition, mixtures of naturally occurring nucleic acids and analogs can be made; alternatively, mixtures of different nucleic acid analogs, and mixtures of naturally occurring nucleic acids and analogs may be made.

The nucleic acids may contain any combination of deoxyribo- and ribo-nucleotides, and any combination of bases, both naturally occurring and synthetic, including uracil, adenine, thymine, cytosine, guanine, inosine, xanthine, hypoxanthine, isocytosine, isoguanine, etc. A preferred embodiment utilizes isocytosine and isoguanine in nucleic acids designed to be complementary to other probes, rather than target sequences, as this reduces non-specific hybridization, as is generally described in U.S. Pat. No. 5,681,702. As used herein, the term "nucleoside" includes nucleotides as well as nucleoside and nucleotide analogs, and modified nucleosides such as amino modified nucleosides or phosphoramidite nucleosides. In addition, "nucleoside" includes non-naturally occurring analog structures. Thus for example the individual units of a peptide nucleic acid, each containing a base, are referred to herein as a nucleoside.

The stepwise synthesis of nucleic acids is well known, and generally involves the stepwise addition of protected, activated nucleoside monomers to a solid support, followed by deprotection steps and washing steps. See generally Gait, Oligonucleotide Synthesis: A Practical Approach, IRL Press, Oxford, UK 1984; incorporated by reference. This is generally done either with phosphoramidite or H-phosphonate nucleosides. This is generally done in one of two ways. First, the 5' position of the ribose is protected with 4',4-dimethoxytrityl (DMT) followed by reaction with either 2-cyanoethoxy-bis-diisopropylaminophosphine in the presence of diisopropylammonium tetrazolide, or by reaction with chlorodiisopropylamino 2'-cyanoethoxyphosphine, to give the phosphoramidite as is known in the art; although other techniques may be used as will be appreciated by those in the art. See Gait, supra; Caruthers, Science 230:281 (1985), both of which are expressly incorporated herein by reference.

In a preferred embodiment, the reverse tilt method is used to synthesize small organic molecules. As will be appreciated by those in the art, the literature contains numerous examples of the synthesis of a variety of small molecules, particularly libraries of small molecules on solid-phase supports; see for example Pavia et al. Bioorganic & Medicinal Chemistry 1996 4(5):659-666; Liskamp et al., Bioorganic & Medicinal Chemistry 19964(5):667-672; Tong et al., Bioorganic & Medicinal Chemistry 1996 4(5):693-698; Houghten et al., Bioorganic & Medicinal Chemistry 1996 4(5):709-715, Freier et al., Bioorganic & Medicinal Chemistry 1996 4(5): 717-725; Bolton et al., Tetrahedron Letters 1996 37(20)3433-3436; all of which are hereby expressly incorporated by reference.

In addition, for all the reverse tilt embodiments herein, it may be desirable to use linkers to attach the first building blocks to the surface.

Accordingly, the invention provides methods of synthesis using reverse tilt centrifugation. In this embodiment, a reaction vessel or array of vessels are provided that comprise either a pre-functionalized first building block or the chemistry to attach the first building block of the molecule to be made. Subsequently, a plurality of building block addition steps are performed, all of which involve repetitive execution of the following substeps, and in a sequence chosen to synthesize the desired compound. First a sufficient quantity of a solution containing the building block moiety selected for addition is accurately added to the reaction vessels so that the building block moiety is present in a molar excess to the intermediate compound. The reaction is triggered and promoted by activating reagents and other reagents and solvents as needed, which are also added to the reaction vessel. The reaction vessel is then incubated at a controlled temperature for a time, typically between 5 minutes and 24 hours, sufficient for the building block addition reaction or transformation to go to substantial completion. Optionally, during this incubation, the reaction vessel can be intermittently agitated or stirred. Finally, in a last substep of building block addition, the reaction vessel is prepared for addition of the next building block by removing the reaction fluid using the "reverse tilt" centrifugation steps outlined herein and thorough washing and reconditioning as needed. Washing typically involved three to seven cycles of adding and removing a wash solvent. Optionally, during the addition steps, multiple building blocks can be added to one reaction vessel in order to synthesize a mixture of compound intermediates attached to one reaction vessel. After the desired number of building block addition steps, the final compound is present in the reaction vessel. It can then be optionally cleaved from the reaction vessel support; alternatively, the reaction vessels themselves can be used in subsequent reactions. A variety of exemplary reactions are outlined in WO99/25470, hereby incorporated by reference, and include reactions for peptide and synthetic peptides, benzodiazepine and derivatives, peptoids, N-substituted polyamide monomers. Exemplary building blocks and reagents are amino acids, nucleic acids, other organic acids, aldehydes, alcohols, and so forth, as well as bifunctional compounds.

The present invention also provides apparatus for organic synthesis as outlined herein. The apparatus of the invention comprise a variety of components, including a centrifuge and a rotor. In general, the rotor comprises at least one holder, and preferably a plurality of holders, that each will hold at least a first reaction vessel, and preferably a plurality of reaction vessels.

As will be appreciated by those in the art, the reaction vessels can be configured in a variety of ways. In a preferred embodiment, the reaction vessels are in the form of an array of vessels such as a microtiter plate that contains the individual reaction vessels. Particularly preferred configurations are 96-well and 384-well microtiter plates.

As will be appreciated by those in the art, one of the important aspects of the invention is that one or more liquid phases are expelled from the reaction vessels upon centrifugation. Accordingly, there are two main ways the system may be configured to allow the collection of the expelled liquids.

In a preferred embodiment, the holders adapted to attaching a microtiter plate to a centrifuge rotor can have or comprise a series of collecting pockets to collect and retain the liquid expelled from the vessels during centrifugation. These collecting pockets can comprise one or more indentations or grooves having a volume sufficient to collect and retain any expelled liquid.

In an alternative preferred embodiment, the holder does not have collecting pockets. In the latter situation, the liquid expelled is deposited on the walls of the centrifuge. In this embodiment, the centrifuge is configured such that there is a collecting pocket or reservoir, generally in the bottom of the centrifuge, such that gravity flow of the expelled liquids causes the liquids to pool in the pocket. This may be periodically emptied as needed, and can comprise a port or valve that allows drainage.

Alternatively, the centrifuge is configured to have a tube or pipe leading to a waste reservoir; this tube is also generally at the bottom of the centrifuge. The gravity flow of the expelled liquids can then lead to collection of the waste outside the centrifuge.

In a preferred embodiment, the holder(s) hold the reaction vessels in a tilted position. The holder(s) may either hold one or more of the reaction vessels in a fixed tilted position or in a position in which the angle of tilt can be changed flexibly.

As outlined herein, the tilt of the rotor can be towards the axis of rotation, resulting in the retention of a phase of the reaction. Alternatively, when the synthetic reaction is done on material firmly attached to the reaction vessel (e.g. with a force such that it will not be expelled during the centrifugation) or when the reaction is done on the reaction vessel itself, the tilt of the rotor can be away from the axis of rotation ("reverse tilt") as described herein.

In a preferred embodiment, each holder contains only one set or array of reaction vessels. Thus, for example, the holder may contain grooves or rails to position the reaction vessels, e.g. microtiter plate, in the holders. Alternatively, the reaction vessels may be "stacked" or "layered". However, placing single sets or arrays of reaction vessels such as individual microtiter plates on the centrifuge perimeter has an advantage of simple interfacing with liquid distribution automats (such as Packard Canberra, Tecan, Hamilton, and others). A liquid distribution device can be placed onto the top of a centrifugal synthesizer. Particularly preferred are liquid distribution systems for simultaneous dispensing in a format that fits the reaction vessel configuration; for example, when the reaction vessels are in the form of a 96 well microtiter plate, the liquid distribution system is preferably a 96 channel device.

The liquid distribution system can also comprise a set of reservoirs and tubes for delivery; for example, the liquid distribution system can have a 96 channel liquid distributor that can deliver solvent or solutions of reagents from different bottles into the plate positioned under the needles of the distributor. For example, for nucleic acid synthesis, preferred embodiments include separate reagent bottles for each nucleoside.

In a preferred embodiment, the liquid distribution system is an integrated system; that is, the liquid is distributed into the reaction vessels when they are present in the centrifuge; the reaction vessels are not removed from the centrifuge for addition of reagents. In general, the liquid distribution system is an integral part of the centrifuge; the liquid is delivered without removing the lid of the centrifuge.

In addition, the apparatus of the invention can further comprise a processor or computer to control the synthesis of the moieties. For example, a computer may be used that processes a program of instructions of stepwise additions of liquid phases, reagents, solvents, washes, etc. to the reaction vessels, followed by centrifugation steps for removal of liquids from the reaction vessels. Thus, the present invention provides methods executed by a computer under the control of a program, the computer including a memory for storing the program. The program is directed to the addition of reagents to the reaction vessels using the liquid distribution system, allowing incubation as needed, and removing unreacted reagents and liquid by centrifugation for a defined time at a defined speed, with wash steps and repetition as required.

In addition to the components mentioned above, the centrifuge may also comprise additional components. For example, the centrifuge can comprise a sensor to signal the computer and liquid distribution system when a set of reaction vessels in a particular orientation, and a motor to rotate the rotor into the correct orientation for liquid delivery, also in control of the computer. Furthermore, in the case of adjustable tilt holders or rotors, the centrifuge can utilize a control and a sensor to control the degree of tilt.

The integrated device is useful as a "centrifugation synthesizer" for fluorous phase synthetic processes.

The methods and apparatus of the invention find use in a number of applications, as outlined herein.

In a preferred embodiment, the methods and apparatus of the present invention are advantageously useful for the manual or automated preparation of combinatorial libraries or megaarrays of compounds by fluorous phase organic synthesis. As is well known to those skilled in the art, such combinatorial libraries or megaarrays have numerous uses, in particular, for the selection of pharmaceutical lead compounds, for the optimization of pharmaceutical lead compounds and for the identification and/or isolation of pharmaceutical drugs. The methods and apparatus of the invention for liquid/liquid phase separation can also advantageously be used for parallel extraction and purification of compound arrays synthesized or obtained by other methods. Other applications in analytical chemistry (extraction, desalting or other means of parallel preparations of samples), biochemistry (parallel processing of samples) are envisioned.

The use of complete removal of liquid from the arrays of vessels can be applied in the biological screening where binding to the surface of the vessels (modified surface by attached reagent or cell culture) is investigated. In this case the tilt of the vessel during the centrifugation is "reversed", i.e. no "pocket" is formed during the centrifugation. In this case, for example, any number of binding assays may be done. For example, ELISA type assays are frequently done in a microtiter plate format, where antibodies are attached using a variety of known chemistries. The addition of sample(s) and additional reagent components, with washing as required, may utilize the present invention. Furthermore, in this embodiment, the apparatus may comprise additional components such as fluorescence readers.

Similarly, reverse tilt reactions can be used in synthetic reactions as outlined above, with particular emphasis on nucleic acid and peptide synthesis.

EXAMPLE

Figure 5:
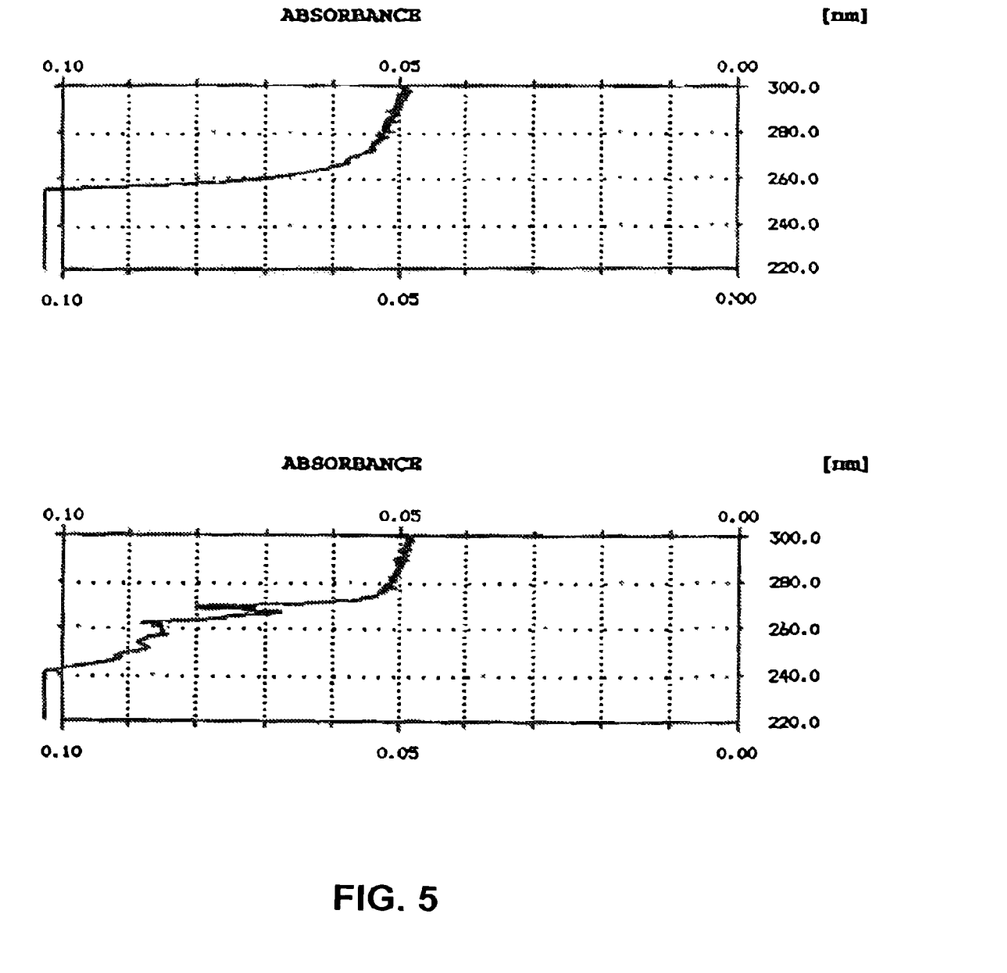
FIG. 5 shows the UV spectra of wells before and after two steps of parallel extraction proving complete elimination of contamination by aromatic hydrocarbon.

Removal of Upper Layer Liquid Phase without Transfer of Lower Layer Liquid Phase Ten percent solution of ethanol in water saturated with toluene was distributed into wells of microtiterplate (40 µL per well). Ethyl acetate (150 µL) was repeatedly distributed into the wells and microtiterplates were shaken for 1 minute and centrifugated in tilted arrangement. FIG. 5 shows UV spectra of wells before and after two steps of parallel extraction proving complete elimination of contamination by aromatic hydrocarbon.

What is claimed is:

1. An apparatus for separating fluids from solid phase components, said apparatus comprising a plurality of vessels, said vessels arranged around an axis of rotation such that fluid flows away from the axis of rotation while the vessels are rotating, wherein beads are firmly attached to said vessels so as to be retained in the vessels when the vessels are rotating about said axis of rotation.

2. The apparatus of claim 1, wherein the vessels comprise microtiter plates.

3. The apparatus of claim 1, wherein the vessels are present in a rotor.

4. The apparatus of claim 3 further comprising a liquid distribution system configured to deliver liquids to the plurality of vessels when the vessels are present in the rotor.

5. The apparatus of claim 3, wherein the vessels are positioned in holders.

6. The apparatus of claim 1, wherein each of the vessels comprises at least one open end pointed away from the axis of rotation.

7. The apparatus of claim 1, wherein the beads comprise microbeads having a diameter of approximately 30 to 300 microns.

8. The apparatus of claim 1, wherein the beads are functionalized for the attachment of a chemical building block.

9. The apparatus of claim 8, wherein the chemical building block comprises a nucleoside.

10. The apparatus of claim 8, wherein the chemical building block comprises an amino acid.

11. The apparatus of claim 1, wherein said plurality of vessels further comprises a fluid.

12. The apparatus of claim 11, wherein said fluid comprises water.

13. The apparatus of claim 1 further comprising a liquid distribution system configured to deliver liquids to the plurality of vessels.

14. The apparatus of claim 13, wherein the liquid distribution system comprises 96 channels configured to deliver the liquids to 96 vessels.

15. A method of separating fluid from solid phase components, said method comprising the steps of:
(a) providing a plurality of vessels containing a fluid, said vessels arranged around an axis of rotation such that fluid flows away from the axis of rotation while the vessels are rotating, wherein beads are firmly attached to said vessels so as to be retained in the vessels when the vessels are rotating about said axis of rotation, and
(b) rotating the vessels around the axis of rotation, thereby separating fluid from solid phase components.

16. The method of claim 15, wherein the beads comprise microbeads having a diameter of approximately 30 to 300 microns.

17. The method of claim 15, wherein the beads are functionalized for the attachment of a chemical building block.

18. The method of claim 17, wherein said building block is a nucleoside.

19. The method of claim 15, wherein said fluid comprises an organic solvent.

20. The method of claim 19, wherein said organic solvent comprises water.

21. The method of claim 19, wherein said vessels comprise a chemical building block.

22. The method of claim 21 further comprising a step of providing a wash fluid to said vessel subsequent to step (b).

23. The method of claim 21 further comprising cleaving a final compound from said vessels.

24. The method of claim 15, wherein the vessels comprise microtiter plates.

25. The method of claim 15, wherein each of the vessels comprises at least one open end pointed away from the axis of rotation.

26. The method of claim 15 further comprising repeating steps (a) and (b).

27. The method of claim 15 further comprising a step of distributing the fluid to the plurality of vessels, thereby providing the plurality of vessels containing the fluid.

28. The method of claim 15, wherein the vessels comprise linkers for the attachment of a chemical building block.

* * * * *